(12) United States Patent
Nakamura et al.

(10) Patent No.: US 6,605,736 B1
(45) Date of Patent: *Aug. 12, 2003

(54) PROCESS FOR THE PREPARATION OF CONDENSED PHOSPHORIC ESTERS

(75) Inventors: Shin Nakamura, Aichi (JP); Kazuo Noguchi, Aichi (JP); Taku Fujisawa, Aichi (JP); Takafumi Ohkawa, Aichi (JP)

(73) Assignee: Daihachi Chemical Industry Co., Inc., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/019,462

(22) PCT Filed: Nov. 8, 1999

(86) PCT No.: PCT/JP99/06216

§ 371 (c)(1), (2), (4) Date: Apr. 15, 2002

(87) PCT Pub. No.: WO01/00636

PCT Pub. Date: Jan. 4, 2001

(30) Foreign Application Priority Data

Jun. 28, 1999 (JP) .......................................... 11/182605

(51) Int. Cl.⁷ .................................................. C07F 9/02
(52) U.S. Cl. .......................................... 558/92; 568/16
(58) Field of Search ............................... 558/92; 568/16

(56) References Cited

U.S. PATENT DOCUMENTS

| 2,520,090 | A | 8/1950 | Barrett |
| 6,420,465 | B1 * | 7/2002 | Janke et al. ................. 524/126 |

FOREIGN PATENT DOCUMENTS

| JP | 53-98355 | 8/1978 |
| JP | 63-227632 | 9/1988 |
| JP | 9-249768 | 9/1997 |

* cited by examiner

Primary Examiner—Joseph K. McKane
Assistant Examiner—Robert Shiao
(74) Attorney, Agent, or Firm—Snell & Wilmer, LLP

(57) ABSTRACT

A condensed phosphoric ester having a very low content of volatile components is provided by a process including a first step of reacting a phosphorus oxytrihalide with a bisphenol-based compound to prepare a phosphorohalidate; a second step of removing unreacted phosphorus oxytrihalide; and a third step of reacting the phosphorohalidate with a monophenol-based compound at a specific ratio.

8 Claims, No Drawings

PROCESS FOR THE PREPARATION OF CONDENSED PHOSPHORIC ESTERS

TECHNICAL FIELD

The present invention relates to a process for preparing a condensed phosphoric ester. More specifically, the present invention relates to a process for preparing a condensed phosphoric ester having a low content of volatile components, which is excellent as a flame retardant for resins.

BACKGROUND ART

Conventionally, various types of flame retardants are used for flame retardation of inflammable plastic materials, for example, halogen compounds such as decabromobiphenylether and tetrabromobisphenol A, and low molecular weight phosphorus compounds such as cresyl diphenyl phosphate and triphenyl phosphate.

Today, resin compositions are required to be non-halogenic from an environmental point of view, for example, due to the hazardous effects of dioxin. Flame retardants containing heavy metals cause problems due to their toxicity. Under these circumstances, phosphorus-based flame retardants have now become a target of attention. Among the phosphorus-based flame retardants, aromatic phosphoric ester-based flame retardants are a target of attention for their effectiveness especially in the applications of engineering plastics such as PC/ABS alloys and modified PPE since they have little adverse influence on the environment as well as superb physical properties. Actually, the industrial demand for phosphorus-based flame retardants, especially aromatic phosphoric ester-based flame retardants, is good and continues to increase at a high rate.

However, engineering plastics are molded at a very high temperature and therefore the following problems have occurred. When a low molecular weight monomer-type phosphoric ester such as triphenyl phosphate (TPP) or tricresyl phosphate (TCP) is used, the monomer-type phosphoric ester is thermally decomposed, bleeds out or volatizes during the molding process, which causes defective molding, contamination of the molds or the like.

It is known that use of a high molecular weight condensed phosphoric ester as a flame retardant is effective for avoiding these problems.

For example, Japanese Laid-Open Publication No. 63-227632 discloses a process for preparing a condensed phosphoric ester. According to this process, a condensed phosphoric ester is prepared by reacting a dihydroxy compound such as resorcin, hydroquinone, bisphenol A or the like with phosphorus oxychloride, thereafter removing unreacted phosphorus oxychloride, and then reacting the resultant product with phenol, cresol, xylenol or the like.

This process, however, has the problem that a significant amount, specifically about 4 to 7% by weight of monomer-type phosphoric ester is contained as an impurity, especially when the production is performed on an industrial scale. Therefore, the monomer-type phosphoric ester still volatizes or bleeds out, which causes defective molding, contamination of the molds or the like. As such, it is difficult to obtain a satisfactory molding efficiency.

More specifically, for example, Japanese Laid-Open Publication No. 63-227632 reports, in an example thereof, that a product having a content of a low molecular weight phosphate of equal to or less than 2% by weight was obtained in a small-scale test. However, when this technology is used for large-scale synthesis, the monomer-type phosphoric ester content is about 4 to 7% by weight.

Accordingly, production of a condensed phosphoric ester, especially on an industrial scale, requires that many conditions including the ratio of materials, reaction temperature, and reaction time should be carefully selected in order to reduce the content of the monomer-type phosphoric ester as an impurity.

Until today, details of such conditions have not been studied, and thus the relationship between the conditions and the amount of impurity in the resultant product has not been clarified at all. Especially regarding the ratio of materials, ratios obtained by theoretical calculations based on stoichiometry have been considered to be most efficient in order to reduce the impurity. Therefore, the ratios obtained by stoichiometric calculations have been loyally adopted.

Problems to be Solved by the Invention

An objective of the present invention is to solve the above-described problems by providing a process for stably preparing a condensed phosphoric ester formed from a low molecular weight monomer-type phosphoric ester and having a low content of impurities.

DISCLOSURE OF THE INVENTION

Means for Solving the Problems

The present inventors completed the present invention as a result of performing active studies based on the knowledge that the reaction between condensed phosphoric ester produced by the below-mentioned third step and an unreacted monophenol-based compound causes interesterification and thus produces a monomer-type phosphoric ester as an impurity.

The present invention provides the following processes.

1. A process for preparing a condensed phosphoric ester, comprising:
   a first step of reacting a phosphorus oxytrihalide with a bisphenol-based compound to prepare a phosphorohalidate;
   a second step of removing unreacted phosphorus oxytrihalide remaining after the first step; and
   a third step of reacting the phosphorohalidate with a monophenol-based compound in a stoichiometrically excess amount with respect to the phosphorohalidate,
   wherein the amount of the monophenol-based compound in the third step is greater, by equal to or less than 2 mol %, than the theoretically necessary amount for turning the entire amount of the phosphorohalidate into the condensed phosphoric ester.
2. A process according to aforementioned item 1, wherein the amount of the phosphorus oxytrihalide is equal to or greater than 3.6 mol times with respect to the amount of the bisphenol-based compound.
3. A process according to aforementioned item 1 or 2, wherein the bisphenol-based compound is bisphenol A.
4. A process according to any one of aforementioned item 1, 2 or 3, wherein the condensed phosphoric ester is 2,2-bis{4-[bis(phenoxy)phosphoryl]oxyphenyl}propane.

BEST MODE FOR CARRYING OUT THE INVENTION

Hereinafter, the present invention will be specifically described.

First Step

In the first step, a phosphorus oxytrihalide and a bisphenol-based compound are reacted, thereby preparing a phosphorohalidate.

In the present invention, a phosphorohalidate refers to a compound represented by the following formula (I):

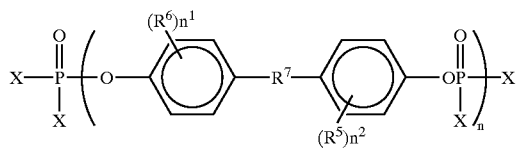

(where X represents a halogen atom, $R^5$ and $R^6$ are the same as or different from each other and represent a hydrogen atom or an alkyl group containing 1 to 3 carbon atoms; $R^7$ represents $—C(CH_3)_2—$, $—SO_2—$ or $CH_2—$; n represents an integer from 1 to 10; and $n^1$ and $n^2$ each represent an integer from 0 to 4.)

Examples of the phosphorus oxytrihalide include phosphorus oxychloride and phosphorus oxybromide.

A bisphenol-based compound refers to a compound containing two phenol groups (—PhOH) in a molecule. Specific examples of the bisphenol-based compound include bisphenol A, bisphenol S, and bisphenol F. A bisphenol A derivative is preferable, and bisphenol A is especially preferable.

The Bisphenol A derivative refers to bisphenol A or a derivative thereof, which is represented by the following formula (A):

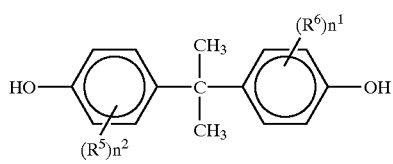

(where $R^5$ and $R^6$ are the same as or different from each other and represent an alkyl group containing 1 to 3 carbon atoms; and $n^1$ and $n^2$ each represent an integer from 0 to 4.)

The usable amount of the phosphorus oxytrihalide and the usable amount of the bisphenol-based compound are not specifically limited.

According to general technical knowledge, it is not preferable that the amount of the phosphorus oxytrihalide is greater than a stoichiometrical reaction amount which is calculated from the amount of the bisphenol-based compound, i.e., 2.0 mol times the amount of the bisphenol-based compound. The reason is that the amount of remaining unreacted phosphorus oxytrihalide necessarily increases, which complicates the operation for recovering the unreacted phosphorus oxytrihalide.

According to the present invention, the amount of the phosphorus oxytrihalide is preferably equal to or greater than 3.6 mol times the amount of the bisphenol-based compound, and more preferably equal to or greater than 4.5 mol times the amount of the bisphenol-based compound.

Here, "mol times" refers to the ratio based on the mol value.

When the amount of the phosphorus oxytrihalide is relatively small, there is an undesirable possibility that a hydrogen halide, produced as a by-product of the reaction of the phosphorus oxytrihalide and the bisphenol-based compound, contacts the bisphenol-based compound and as a result, decomposes the bisphenol-based compound.

The upper limit of the amount of the phosphorus oxytrihalide cannot be determined. When the amount of the phosphorus oxytrihalide is excessive, an unnecessarily large amount of phosphorus oxytrihalide needs to be removed in the second step described below, and decreases the operation efficiency in the reactor and also the productivity. The phosphorus oxytrihalide is preferably used in an amount equal to or less than 8 mol times, and more preferably equal to or less than 6 mol times the amount of the bisphenol-based compound. Still more preferably, the amount of the phosphorus oxytrihalide and the bisphenol-based compound are adjusted within the above-mentioned ranges so that the concentration of the hydrogen halide in the reaction solution is equal to or less than 5%.

According to the present invention, a catalyst can be used. Usable catalysts include, for example, Lewis acid-based catalysts such as aluminum chloride, magnesium chloride and titanium tetrachloride.

The other conditions, for example, the reaction temperature, reaction time and reduction in pressure can be appropriately selected in accordance with the type of the intended condensed phosphoric ester, condensation degree, and type and scale of the apparatus used. The temperature is preferably 80 to 130° C., and more preferably 80 to 120° C. It is acceptable to start with a temperature lower than 80° C. and then raise the temperature to 80 to 130° C. For example, it is acceptable to start with room temperature and then raise the temperature to 80 to 130° C. The reaction time is preferably 3 to 20 hours. Hydrogen halide gas generated by the reaction is preferably captured by water.

An organic solvent can be used when necessary although it is not usually necessary. For example, aromatic group-based organic solvents including toluene, xylene, and dichlorobenzene and aliphatic group-based organic solvents including hexane and heptane are usable.

When it is necessary to prevent the resultant product from being colored, a phosphorus-based compound such as, for example, triphenyl phosphite or tri(2,6-di-t-butyl) phosphite; a hindered phenol-based compound such as, for example, 2,6-di-t-butyl-p-cresol (BHT) or 2-methyl-6-t-butyl-p-cresol; or the like can be added as a coloring prevention agent.

Second Step

In the second step, the phosphorus oxytrihalide remaining unreacted after the first step is removed.

The removal of the phosphorus oxytrihalide can be performed using any known method.

The removal of the unreacted phosphorus oxytrihalide is usually performed at normal pressure or under reduced pressure. Performing the third step described below in the state where the phosphorus oxytrihalide is not sufficiently removed, i.e., in the state where phosphorus oxytrihalide remains, causes generation of a monomer-type phosphoric ester. Therefore, it is preferable to remove and recover the maximum possible amount of the phosphorus oxytrihalide. Preferable conditions for removing and recovering the phosphorus oxytrihalide are, for example, as follows. The pressure is reduced to equal to or less than 200 mmHg, more preferably equal to or less than 50 mmHg, by a vacuum pump. The recovery temperature is preferably 100 to 200° C., more preferably 100 to 170° C., and still more preferably 100 to 150° C.

Third Step

The third step has an objective of reacting the phosphorohalidate obtained in the first step and the second step with a monophenol-based compound so as to obtain a condensed phosphoric ester.

In the present invention, the condensed phosphoric ester refers to a compound represented by the following formula (II):

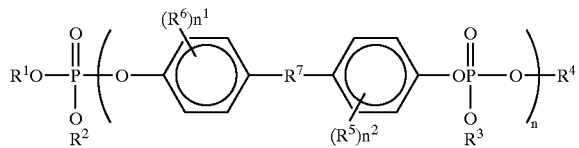

(II)

(where $R^1$, $R^2$, $R^3$ and $R^4$ independently represent an identical or different aryl group containing 6 to 15 carbon atoms; and $R^5$, $R^6$, $R^7$, n, $n^1$ and $n^2$ are the same as those in formula I.)

Examples of the aryl group containing 6 to 15 carbon atoms include phenyl, (o-, m-, p-)methylphenyl, (o-, m-, p-)ethylphenyl, (o-, m-, p-)n-propylphenyl, (o-, m-, p-)isopropylphenyl, (o-, m-, p-)n-butylphenyl, (o-, m-, p-)sec-butylphenyl, (o-, m-, p-)tert-butylphenyl, (2,3-2,4-, 2,5-, 2,6-, 3,4-, 3,5-)dimethylphenyl, (2,3- 2,4-, 2,5-, 2,6-, 3,4-, 3,5-)diethylphenyl, 2-methyl-3-ethylphenyl, 2-methyl-4-ethylphenyl, 2-methyl-5-ethylphenyl, 2-methyl-6-ethylphenyl, 3-methyl-4-ethylphenyl, 3-methyl-5-ethylphenyl, 2-ethyl-3-methylphenyl, 2-ethyl-4-methylphenyl, 2-ethyl-5-methylphenyl, 3-ethyl-4-methylphenyl, (2,3-, 2,4-, 2,5-, 2,6-, 3,4-, 3,5-)di-n-propylphenyl, (2,3-, 2,4-, 2,5-, 2,6-, 3,4-, 3,5-)diisopropylphenyl, (2,3-, 2,4-, 2,5-, 2,6-, 3,4-, 3,5-)di-n-butylphenyl, (2,3-, 2,4-, 2,5-, 2,6-, 3,4-, 3,5-)di-sec-butylphenyl, (2,3-, 2,4-, 2,5-, 2,6-, 3,4-, 3,5-)di-tert-butylphenyl, (2,3,6-, 2,3,5-, 2,3,4-, 2,4,5-, 2,4,6-, 3,4,5-) trimethylphenyl, (2,3,6-, 2,3,5-, 2,3,4-, 2,4,5-, 2,4,6-, 3,4,5-) triethylphenyl, (2,3,6-, 2,3,5-, 2,3,4-, 2,4,5-, 2,4,6-, 3,4,5-) tripropylphenyl, and naphtyl. Here, "(o-, m-, p-)" indicates that substituents independently exist in either positions of o- (ortho), m-(meta) or p- (para) on a benzene ring. "(2,3-, 2,4-, 2,5-, 2,6-, 3,4-, 3,5-)" indicates that substituents independently exist in positions 2,3-, 2,4-, 2,5-, 2,6-, 3,4-, or 3,5- on a benzene ring. "(2,3,6-, 2,3,5-, 2,3,4-, 2,4,5-, 2,4,6-, 3,4,5-)" indicates that substituents independently exist in positions 2,3,6-, 2,3,5-, 2,3,4-, 2,4,5-, 2,4,6-, or 3,4,5- on a benzene ring.

Specific examples of the condensed phosphoric ester represented by formula (II) include 2,2-bis{4-[bis(phenoxy)phosphoryl]oxyphenyl)}propane, 2,2-bis{4-[bis (methylphenoxy)phosphoryl]oxyphenyl}propane, 2,2bis{4-[bis (dimethylphenoxy)phosphoryl]oxyphenyl}propane, and 2,2-bis{4-[bis(methylethylphenoxy) phosphoryl] oxyphenyl}propane which are made from bisphenol A; 2,2-bis{4-[bis(phenoxy)phosphoryl]oxyphenyl}methane, 2,2-bis{4-[bis(methylphenoxy)phosphoryl] oxyphenyl}methane, and 2,2-bis{4-[bis(dimethylphenoxy) phosphoryl]oxyphenyl}methane, which are made from bisphenol F; and 2,2-bis{4-[bis(phenoxy)phosphoryl] oxyphenyl}sulfone, 2,2-bis{4-[bis(methylphenoxy) phosphoryl]oxyphenyl}sulfone, and 2, 2-bis{4- [bis (dimethylphenoxy)phosphoryl]oxyphenyl}sulfone which are made from bisphenol S.

A monophenol-based compound refers to phenol or a substituted phenol containing one phenolic hydroxyl group.

Examples of the monophenol-based compound include phenol, (o-, m-, p-)methylphenol, (o-, m-, p-)ethylphenol, (o-, m-, p-)n-propylphenol, (o-, m-, p-)isopropylphenol, (o-, m-, p-)n-butylphenol, (o-, m-, p-)sec-butylphenol, (o-, m-, p-)tert-butylphenol, methylphenol, (2,3- 2,4-, 2,5-, 2,6-, 3,4-, 3,5-)dimethylphenol, (2,3- 2,4-, 2,5-, 2,6-, 3,4-, 3,5-) diethylphenol, 2-methyl-3-ethylphenol, 2-methyl-4-ethylphenol, 2-methyl-5-ethylphenol, 2-methyl-6-ethylphenol, 3-methyl-4-ethylphenol, 3-methyl-5-ethylphenol, 2-ethyl-3-methylphenol, 2-ethyl-4-methylphenol, 2-ethyl-5-methylphenol, 3-ethyl-4-methylphenol, (2,3-, 2,4-, 2,5-, 2,6-, 3,4-, 3,5-)di-n-propylphenol, (2,3-, 2,4-, 2,5-, 2,6-, 3,4-, 3,5-) diisopropylphenol, (2,3-, 2,4-, 2,5-, 2,6-, 3,4-, 3,5-)di-n-butylphenol, (2,3-, 2,4-, 2,5-, 2,6-, 3,4-, 3,5-)di-sec-butylphenol, (2,3-, 2,4-, 2,5-, 2,6-, 3,4-, 3,5-)di-tert-butylphenol, (2,3,6-, 2,3,5-, 2,3,4-, 2,4,5-, 2,4,6-, 3,4,5-) trimethylphenol, (2,3,6-, 2,3,5-, 2,3,4-, 2,4,5-, 2,4,6-, 3,4,5-) triethylphenol, (2,3,6-, 2,3,5-, 2,3,4-, 2,4,5-, 2,4,6-, 3,4,5-) tripropylphenol, and naphtol. Phenol is especially preferable. One monophenol-based compound or a combination of two or more monophenol-based compounds can be used.

In the present invention, a monomer-type phosphoric ester refers to a triester produced by the reaction of a phosphorus oxytrihalide and a monophenol-based compound. Specific examples of the monomer-type phosphoric ester include triphenyl phosphate, tricresyl phosphate[(o-, m-, p-)methylphenyl phosphate], and trixylyl phosphate[(2, 3-, 2,4-, 2,5-, 2,6-, 3,4-, 3,5-)dimethylphenyl phosphate].

In the third step, an excess amount of monophenol-based compound is reacted with a phosphorohalidate. The amount of the monophenol-based compound is greater by an excess ratio of equal to or less than 2 mol % than the amount which is theoretically necessary for turning the entire amount of the phosphorohalidate contained in the reaction mixture after the second step into a condensed phosphoric ester.

Thus, the production of a monomer-type phosphoric ester as a by-product which is caused by interesterification of the condensed phosphoric ester produced and the monophenol-based compound can be suppressed without reducing yield or quality. Considering that interesterification of the condensed phosphoric ester and the monophenol-based compound is likely to occur especially in industrial, large scale production due to the long reaction time, the process of the present invention which can suppress the production of a monomer-type phosphoric ester as a by-product is very advantageous.

Here, the term "industrial scale" indicates that the total amount of the monophenol-based compound and the phosphorohalidate which are reacted with each other is an amount used in usual industrial production. Specifically, industrial scale is preferably equal to or greater than 5 liters, more preferably equal to or greater than 30 liters, still more preferably equal to or greater than 100 liters, and especially preferably equal to or greater than 300 liters.

The total amount of the monophenol-based compound and the phosphorohalidate which are reacted with each other is specifically preferably equal to or less than 20000 liters, and more preferably equal to or less than 10000 liters due to restrictions caused by, for example, the reaction apparatus.

When the amount of the monophenol-based compound is smaller than the theoretical amount stoichiometrically calculated, unreacted phosphorohalidate will inevitably remain, which causes problems which complicate the purification and post-processing steps.

When the amount of the monophenol-based compound is the theoretical amount stoichiometrically calculated, the reaction is likely to be incomplete. As a result, unreacted phosphorohalidate remains, which causes the problems of, for example, the phosphorohalidate remaining in the product as an impurity or complicating the purification and post-processing steps.

An excess amount of the monophenol-based compound is not preferable since the amount of the monomer-type phosphoric ester produced as a by-product is increased. Therefore, the monophenol-based compound needs to be greater than the stoichiometrically theoretical amount by equal to or less than 2.0 mol %, preferably equal to or less than 1.8 mol %, more preferably equal to or less than 1.6 mol %, and especially preferably equal to or less than 1.5 mol %.

The stoichiometrically theoretical amount necessary for turning the entire amount of the phosphorohalidate into a condensed phosphoric ester refers to the amount which is necessary for substituting all the halogen atoms contained in the phosphorohalidate with arylester groups. For example, in the case where n=1 in formula (I) above, such an amount of the monophenol-based compound is 4 mol with respect to 1 mol of the phosphorohalidate. In the case where n=2, such an amount of the monophenol-based compound is 5 mol with respect to 1 mol of the phosphorohalidate. In the case where n=3, such an amount of the monophenol-based compound is 6 mol with respect to 1 mol of the phosphorohalidate.

Here, the excess ratio is a value obtained by subtracting the stoichiometrically theoretical mol value from the used mol value of the monophenol-based compound, dividing the resultant value by the stoichiometrically theoretical mol value to obtain a ratio, and then multiplying the ratio by 100 so as to be represented by a percentage.

The lower limit of the amount of the monophenol-based compound cannot be exactly determined since it varies in accordance with, for example, the type of the condensed phosphoric ester and the reaction conditions. The lower limit is preferably equal to or greater than 0.2 mol %, more preferably equal to or greater than 0.3 mol %, especially preferably equal to or greater than 0.4 mol %, and still more preferably equal to or greater than 0.5 mol %.

The other reaction conditions (e.g., the reaction temperature, reaction time, reduction in pressure, the time to add the monophenol-based compound) are appropriately selected as desired. For example, the reaction temperature is preferably 90 to 170° C., more preferably 120 to 170° C., and especially preferably 140 to 160° C. The temperature is maintained preferably above 120° C, more preferably at 120 to 170° C. and especially preferably at 140 to 160° C., preferably for 30 minutes to 5 hours, more preferably for 30 minutes to 4 hours, and especially preferably for 1 to 3 hours. The hydrogen halide generated during the reaction and remaining after the reaction is preferably recovered at normal pressure or low pressure. The hydrogen halide can be, for example, captured by water to be recovered.

A condensed phosphoric ester prepared in this manner usually contains a great amount of impurities including partially reacted components, unreacted components, and remaining catalysts. Therefore, the impurities are removed from the crude condensed phosphoric ester by known purification methods such as neutralization, water rinsing, steam distillation or the like.

When, for example, a method using an epoxy compound is adopted for purification, the epoxy compound is added to an —OH group of a partially reacted component and then selective hydrolysis is performed. Thus, the partially reacted product can be converted into phosphoric acid. By washing the phosphoric acid with hot water, the phosphoric acid components can be removed so as to reduce the acid value of the product.

A product obtained in this manner is a high quality condensed phosphoric ester having a very low content of monomer-type phosphoric ester.

Such a high quality condensed phosphoric ester can be used for various types of resins as a flame retardant.

Specifically, the high quality condensed phosphoric ester can be used for, for example, the following resins: thermoplastic resins such as polyethylene-based resins, polypropylene-based resins, polybutadiene-based resins, polystyrene-based resins, polyphenylene ether-based resins, polycarbonate-based resins, ABS (acrylonitrile-butadiene-styrene)-based resins, high impact styrene-based resins, SAN (styrene-acrylonitrile)-based resins, polyamide-based resins, polyester-based resins, polyphenylene sulfide-based resins, polyacrylic resins, polymethacrylic resins, and the like; and thermosetting resins such as epoxy-based resins, polyurethane-based resins, polyimide-based resins, phenol-based resins, novolac-based resins, polyetherimide-based resins, melamine-based resins, urea-based resins and the like.

A condensed phosphoric ester obtained by a process of the present invention can be especially advantageously used for a resin having a high molding temperature, for example, a resin moldable at a temperature of equal to or greater than 160° C. in one embodiment, a resin moldable at a temperature of equal to or greater than 180° C. in a more preferable embodiment, and a resin moldable at a temperature of equal to or greater than 200° C. in an especially preferable embodiment.

When a condensed phosphoric ester obtained by a process of the present invention is added to any of the above-listed resins as a flame retardant, a high quality molded product having excellent resistance against heat and resistance against coloring can be obtained without generating gas despite the high process temperature during the molding process of the resin using a molding apparatus.

A condensed phosphoric ester obtained by a process of the present invention is added to a resin and molded. As result, any desired flame retardant molded product is provided.

For adding the flame retardant to the resin and for molding the resin supplied with the flame retardant, any known method is usable.

For example, the flame retardant and the resin can be melted and kneaded using a multi-purpose kneading apparatus such as a single-screw extruder, a twin-screw extruder, a Banbury mixer, a kneader, a mixer, a roll or the like and mixed with each other. Alternatively, a molding apparatus such as an extruding molding apparatus can be used to produce a plate-like, sheet-like, or film-like molded product. Thus, a desired molded product is obtained.

Examples

Hereinafter, preferable examples will be described, but the present invention is not limited to these examples.

In the examples, the content of the monomer-type phosphoric ester in each product was measured by high-performance liquid chromatography (device: LC10AD, column: SilicaODS-80TM, oven: CTO-10A, eluant: methanol:water=8:2 (v/v), flow rate: 0.8 ml/min., detector: SPD10A, UV frequency of the detector: 254 nm). In the examples, "%" represents "% by weight" unless otherwise specified.

Example 1

An 8000 L reaction device including a stirrer, a thermometer, a dripper, a hydrochloric acid recovery device and a condenser (30° C.) was filled with 6631 kgs (43.2 kmol) of phosphorus oxychloride, 1827 kgs (8 kmol) of bisphenol A and 18.4 kgs of magnesium chloride. These materials were heated to 105° C. over 6 hours while being stirred, and then reacted for another 3 hours. Hydrochloric acid generated was recovered by the hydrochloric acid recovery device (amount recovered: 562 kgs).

Then, treatment was performed at a temperature of 130° C. and a pressure of 50 mmHg for 5 hours in a nitrogen atmosphere. As a result, unreacted phosphorus oxychloride (4170 kgs) was recovered. The concentration of chlorine in the resultant reaction mixture was 30.4%. 2994 kgs (excess ratio: 1%) of phenol was added to 3683 kgs of the resultant reaction mixture over 6 hours at 150° C. and normal pressure, and then reaction was continued for another 1 hour. Hydrochloric acid generated was recovered by the hydrochloric acid recovery device (amount recovered: 1103 kgs). Then, the hydrochloric acid remaining in the system was completely removed at 150° C. and 10 mmHg over 1 hour. Thus, 5496 kgs of crude condensed phosphoric ester was obtained.

1200 kgs of toluene was added to the crude condensed phosphoric ester, and the mixture was washed with an aqueous solution of hydrochloric acid. Then, the organic phase containing the crude condensed phosphoric ester was treated with propylene oxide. After the resultant substance was repetitively rinsed with water, toluene was recovered by distillation under reduced pressure. Then, unreacted phenol was removed by steam distillation. As a result, 5440 kgs of condensed phosphoric ester (2,2-bis{4-[bis(phenoxy) phosphoryl]oxyphenyl}propane was obtained. The content of the monomer-type phosphoric ester (TPP) in the resultant product was 1.6%, and the acid value (KOH/mg) thereof was 0.04.

Comparative Example 1

A condensed phosphoric ester was prepared in a similar process to that of the example except that the amount of the phosphorus oxychloride was 4421 kgs (28.8 kmol) and the amount of the phenol was 3083 kgs (excess ratio: 4%). The content of the monomer-type phosphoric ester (TPP) in the resultant product was 4.5%, and the acid value (KOH/mg) thereof was 0.04.

Comparative Example 2

A condensed phosphoric ester was prepared in a similar process to that of the example except that the amount of the phenol was 3083 kgs (excess ratio: 4%). The content of the monomer-type phosphoric ester (TPP) in the resultant product was 3.5%, and the acid value (KOH/mg) thereof was 0.04.

INDUSTRIAL APPLICABILITY

According to a process for preparing a condensed phosphoric ester of the present invention, the content of the monomer-type phosphoric ester can be reduced to equal to or less than 3% by weight without reducing the yield of the products. Accordingly, a condensed phosphoric ester prepared by the process of the present invention is excellent in heat resistance and volatility. When used as a plasticizer or a flame retardant for a resin, the condensed phosphoric ester prepared by the process of the present invention has the advantages of preventing generation of hazardous gas and contamination of the molds during the molding, and reduction in the heat resistance of the molded product. Among these advantages, improved prevention of contamination of the molds is industrially especially advantageous since it increases the number of continuous shots and thus reduces the production costs.

What is claimed is:

1. A process for preparing a condensed phosphoric ester, comprising:

a first step of reacting a phosphorus oxytrihalide with a bisphenol-based compound to prepare a phosphorohalidate;

a second step of removing unreacted phosphorus oxytrihalide remaining after the first step; and a third step of reacting the phosphorohalidate with a monophenol-based compound in a stoichiometrically excess amount with respect to the phosphorohalidate, wherein the amount of the monophenol-based compound in the third step is greater, by equal to or less than 2 mol %, than the theoretically necessary amount for turning the entire amount of the phosphorohalidate into the condensed phosphoric ester.

2. A process according to claim 1, wherein the amount of the phosphorus oxytrihalide is equal to or greater than 3.6 mol times with respect to the amount of the bisphenol-based compound.

3. A process according to claim 1, wherein the bisphenol-based compound is bisphenol A.

4. A process according to claim 2, wherein the bisphenol-based compound is bisphenol A.

5. A process according to claim 1, wherein the condensed phosphoric ester is 2,2-bis {4-[bis (phenoxy) phosphoryl] oxyphenyl} propane.

6. A process according to claim 2, wherein the condensed phosphoric ester is 2,2 bis{4-[bis (phenoxy) phosphoryl] oxyphenyl} propane.

7. A process according to claim 3, wherein the condensed phosphoric ester is 2,2-bis{4-[bis (phenoxy) phosphoryl] oxyphenyl} propane.

8. A process according to claim 4, wherein the condensed phosphoric ester is 2,2-bis{4-[bis (phenoxy) phosphoryl] oxyphenyl} propane.

* * * * *